United States Patent [19]

Nader

[11] Patent Number: 5,645,984

[45] Date of Patent: Jul. 8, 1997

[54] PROCESS FOR DEPLETING VIRUSES IN SOLUTIONS AND DETERMINING THEIR DEPLETION RATE

[75] Inventor: Werner Nader, Eppelheim, Germany

[73] Assignee: Sanorell Pharma GmbH & Co. KG, Baiersbronn, Germany

[21] Appl. No.: 456,621

[22] Filed: Jun. 1, 1995

Related U.S. Application Data

[63] Continuation of Ser. No. 934,760, Aug. 4, 1993, abandoned.

[30] Foreign Application Priority Data

Feb. 6, 1990 [DE] Germany .................... 40 03 543.3

[51] Int. Cl.$^6$ ...................................... C12Q 1/70
[52] U.S. Cl. .................... 435/5; 435/29; 435/235.1; 435/948; 210/87; 210/651
[58] Field of Search .................... 435/4, 29, 320.1, 435/803, 948, 235.1, 239, 5; 210/87, 651

[56] References Cited

FOREIGN PATENT DOCUMENTS

| 0302949 | 2/1989 | European Pat. Off. ........ B01D 13/00 |
| 0307373 | 3/1989 | European Pat. Off. . |

OTHER PUBLICATIONS

Bechtel, et al. Virus Removal or Inactivation in Hemoglobin Solutions by Ultrafiltration or Detergent/Solvent Treatment, *Biomat., Art. Cells, Art. Org.* 16(1–3):123–128 (1988). (Exhibit C).

Dulbecco, R. and Ginsberg, H.S., *Virology*, 2nd ed., J.B. Lippincott Co., p. 5 (1986). (Exhibit D).

Hamamoto, J. et al., A Novel Method for Removal of Human Immunodeficiency Virus: Filtration with Porous Polymeric Membranes, *Vox Sang* 56:230–236 (1989). (Exhibit E).

Pschyrembel W., Klinisches Worterbuch, Walter de Bruyter, (1982), p. 926 [in German] (Exhibit F).

Zottola et al. J Dairy Science 70:2013–2021 1987.

Cooper "The Tools of Biochemistry" John Wiley & Sons, New York (1977) pp. 206–208.

Knolle et al Virology vol 123: pp. 271–273 (1964).

Applied and Environmental Microbiology, vol. 52(3), Sep. 1986, Traub et al., "Method for Determining Virus Inactivation During Sludge Treatment Processes", pp. 498–503.

Chemical Abstracts, vol. 117, No. 21, Nov. 23, 1992, Becker et al., "Method for Control of Rate of Removal of Pyrogenic Substances, Especially Viruses, From Organic Materials.", Abstract No. 117:208472x, DE 4,126,034.

*Primary Examiner*—Milton Cano
*Attorney, Agent, or Firm*—John P. White

[57] ABSTRACT

To deplete viruses in organic material, the material to be purified is conveyed through an ultrafilter or an ultrafiltration unit the depletion rate of which is previously determined. The filter or filtration unit is charged with viruses of the family Leviviridae and the viral count is determined before and after filtration and used to derive the depletion rate. The virus depletion can be monitored during the process by following the depletion of a marker.

20 Claims, 1 Drawing Sheet

PROCESS FOR DEPLETING VIRUSES IN SOLUTIONS AND DETERMINING THEIR DEPLETION RATE

This application is a continuation of U.S. Ser. No. 07/934,760, filed Aug. 4, 1993, now abandoned.

The invention relates to a process for depleting viruses and determining the depletion rate of viruses in organic material.

Drugs obtained from cell cultures, organs, or blood of animals or humans are potentially contaminated with viruses pathogenic to animals or humans. Considering the broad range of viruses with which the specimen may be contaminated, it is impossible to test the starting material for all viruses which could be present. Moreover, no reliable or sufficiently sensitive detection method exists for several virus groups. For this reason, it is necessary to conduct a purification or inactivation process which will deplete pathogenic viruses, so that, even in case of a massive infection of starting material or intermediate products, no problems are to be expected. The purification or inactivation process should be so efficient that viruses can be depleted by factors of up to $10^{12}$.

To confirm these depletion rates, material samples must be inoculated with viruses in extremely high concentration ranges (spiking), and the decrease in virus titer checked. Since viruses differ considerably in physicochemical behavior, material to be used in the production process must be inoculated with a spectrum of at least four different virus species. This is a very costly procedure, since viruses potentially pathogenic to humans must also be included. These expensive techniques are described, for example, in Heimburger, Schwinn, Gratz, Lüben, Kumpe and Herchenhahn: Factor VIII concentrate, highly purified and heated in solution, Arzneimittelforschung 31: 619–622, 1981; Mauler and Hilfenhaus: Inactivation of viruses in Factor VIII concentrate by heating in solution, Arzneimittelforschung 34: 1524–1527, 1984; Hilfenhaus, Mauler, Friis and Bauer: Safety of human blood products; inactivation of retroviruses by heat treatment at 60° C., Proc. Soc. Exp. Biol. Med. 178:580–584, 1985, for obtaining coagulation factors from human serum.

Sterile filtration has been applied for a long time for elimination of bacteria in the manufacture of drugs. It is considered a reliable decontamination procedure for these potential pathogens. The sterile filters are thereby inoculated by the manufacturer at random with *Pseudomonas diminuta*, the smallest bacterium known, apart from the Mycoplasma and L-form bacteria. If it is possible to demonstrate a certain depletion rate for this bacterium in sterile filtration in the bacteria challenge test, the production lot is considered safe. This type of procedure is described in Wallhaüser, Praxis der Sterilisation, Thieme Pub., Stuttgart, 1988, pp. 324 ff.

It is also possible to apply filtration techniques to eliminate viruses, whereby the filters used must retain molecules and particles of over 1 million daltons. Such ultrafilters are available in the most varied designs, but, in contrast to sterile filters, they do not represent any absolute filter, i.e., molecules and particles larger than 1 million daltons are not absolutely retained but only mostly so. The retention rate is not only dependent on the filter type, but it can even vary from production lot to production lot. Ultrafilters therefore have not yet been used for virus elimination, but instead at most contribute to the overall depletion of viruses in a production process of several steps (Werner and Langlius-Gane: Meeting the Regulatory Requirements for Pharmaceutical Production of Recombinant DNA Derived Products, Arzneimittel-Forschung, 39: 108–111, 1989). This unreliability of ultrafilters is based on the filter production process. In ultrafilters provided for a specific molecular weight exclusion, for example, larger micropores may always appear, which may be permeable to viruses, for example. Moreover, ultrafilters cannot be tested like microfilters for tightness by the so-called bubble-point process.

The object of the invention was therefore to provide a process for depleting viruses which would attain a depletion rate of at least $10^{12}$. A further object of the invention was to create a process with which the depletion rate for viruses can be determined simply and precisely and which provides information concerning by which filtration process and by how many filtration steps a depletion considered reliable is attained.

This object is attained by a process for depleting viruses in solutions, characterized by the fact that the solution to be purified is passed through a filter or filtration unit, whose depletion rate was previously determined, loading the filter or filtration unit with viruses of the Leviviridae family, determining the virus titer before and after filtration, and determining the depletion rate from this. According to the invention, it is also possible to use other comparable small bacteriophages. These bacteriophages are preferably detectable by simple holes in a bacterial growth.

It is also possible, according to the invention, to conduct ultrafiltration as the only method for a reliable virus depletion without additional purification or inactivation steps, by monitoring the virus depletion rate in the continuous process. If this depletion rate is determined before and after filtration of the production batch, and it is higher than $10^{12}$, virus contamination of the product can be excluded with the greatest certainty. Validation experiments have hitherto been conducted only with viruses pathogenic to animals or even humans. Consequently, validated filters could no longer be used after that, for safety reasons. For this reason, it was then necessary to introduce new filters with possibly different depletion rates. Such validation was therefore only applicable to single filter, and moreover, because of the cost involved, it could be applied only once before or after an example of a depletion. In contrast to this, it is possible, according to the invention, to follow the virus depletion in a continuous process, thus as an in-process control.

According to the invention, the solution to be purified is passed over a filter or filtration unit, whose depletion rate was previously determined. By using viruses of the Leviviridae group as test viruses, it is possible to reliably determine the depletion rate without great expense.

Leviviridae, 23 nm in diameter and with a molecular weight of 1.4 million daltons, are smaller than viruses pathogenic to animals or humans (H. Fraenkel-Conrat: The Viruses, Catalogue, Characterization and Classification. Plenum Press, 1982). They infect only certain $F^+$ strains of the harmless intestinal bacterium *Escherichia coli* and, since they are RNA viruses, they are already hydrolyzed in a short time in 10 mM NaOH, thereby being broken down into their individual molecular components. The smallest viruses pathogenic to animals and/or humans come from the Picarna virus group. They are 27 nm in diameter and weigh 2.5 million daltons. Leviviridae are therefore suitable for validating ultrafilters selected according to size. The filters can be washed with 0.1-M NaOH after that, whereby pyrogens derived from *Escherichia coli* are also eliminated. The filters are then again ready for use in production. Conditions defined for in-process control are thereby satisfied, namely by:

a simple and precise validation process which can be conducted in a short time; and reusability of tested filters without additional contamination of the product.

Moreover, Leviviridae can be cultured to extremely high titers of up to $10^{14}$ pfu/ml and are reliably detected by a simple plate method, even at a concentration of 1 pfu/ml.

For the determination, the filter is inoculated with a virus solution with a titer of over $10^{10}$ pfu/ml. The concentration of phages in the filtrate and retained solution is determined. The determination is done in a known way (for example, according to the top agar method of N. H. Adams (1959), Bacteriophages, Interscience Publishers, New York). The phages are mixed with suitable host bacteria (e.g., *E. coli* 3300, ATCC No. 19853) and applied in a layer of 0.6% agar on plates with nutrient agar (e.g., 1% bactotrypton, 0.5% yeast extract, 0.5% NACl, 0.1 mM $CaCl_2$, 1.5% agar). $10^7$ to $10^{10}$ bacteria and less than 100 phages should be applied per plate. The plates are then incubated at 37° C., after which bacteria growth results after 10 hours. Holes in this growth indicate virus attack. The number of holes shows the virus titer in pfu (plaque-forming units). Since one virus can already cause a plaque, it is also possible to demonstrate 1 virus per ml with standard agar plates. It is thus possible to cover a virus concentration range of from over $10^{14}$ to 1 pfu/ml.

The virus depletion rate then results by determining the virus concentration in the filtrate and in the solution before filtration. By determining the virus titer in the concentrate (i.e., the solution retained before the filtration), it is possible to calculate whether viruses were lost by absorption on the filter or inactivation, which gives the validation process additional reliability.

Since the depletion behavior of filtration membranes can vary considerably, not only from manufacturer to manufacturer but also from production lot to production lot, it is essential to determine the virus depletion rate for each individual filter.

It is preferable to test the filter or filter unit provided for purifying organic material under precisely defined pressure conditions, which are also maintained later in the purification process.

After determination of the depletion rate, elimination of bacteriophages and other residues, such as pyrogens, can be attained by simply rinsing with caustic soda solution, and the filters can then be used for the purification process of organic materials. This is a further advantage of the process according to the invention, since this would not be possible with the use of viruses pathogenic to animals or humans, because of the great danger of contamination with such viruses.

From among the Leviviridae group, the viruses MS2, f2, f4, Qβ, Vk, ST, R17 or comparable strains are preferred.

They are described in H. Fraenkel, Conrat: The Viruses Catalogue, Characterization and Classification, Plenum Press, New York, 1982. The bacteriophage fr is especially preferable to use as a test virus. It is filed under number 15767-B1 at the ATCC. It is described in Knolle and Hoffmann-Berling: Virology 123:271–273, 1964. This phage consists of a round protein-RNA complex in polyhedral form measuring 23 nm in diameter. Its molecular weight is 1.4 million daltons.

In a preferred form of execution, the organic material is purified by ultrafiltration in spiral cartridges. The cartridges are loaded by pump. The virus depletion factor is determined with the test virus and is determined before the cartridges are put into operation. The test solution, containing a known test virus quantity, is filtered through the cartridge in tangential flow under precisely defined pressure conditions. The virus titer in the filtrate is then determined by known techniques. After that, the organic material is purified in the same cartridge with maintenance of the same conditions.

Before use for the process according to the invention, the test viruses are cultured in a known way up to a titer of $10^{14}$. *Escherichia coli* 3300, ATCC No. 19853, for example, is suitable as a host bacterium for the bacteriophages. Culture media for culturing phages are known. A suitable medium is described by Luria and Bertani, for example. It contains 1 L distilled water, 10 g Bactotrypton, 5 g yeast extract, and 5 g NaCl. It has a pH of 7.5, adjusted with NaOH, if necessary. To obtain the viruses, they are precipitated from the culture medium by addition of a precipitating agent, for example polyethylene glycol PEG6000. The viruses are then resuspended in buffer solution and adjusted to the desired titer in the buffer solution. A Tris-HCl buffer of pH 7.5, containing 100 mM NaCl and 3 mM $CaCl_2$, is suitable for the purpose, for example. The titer can be determined by the top agar method. After that, this prepared phage suspension is subjected to the filtration process desired for the organic material. The virus titer is determined after conclusion of this filtration, from which the depletion factor can be calculated. The virus titer is given in pfu (plaque-forming units). It represents the number of plaques caused by the virus infection on the bacterial growth. After rinsing the cartridge with caustic soda solution and neutralizing by rinsing with distilled water, the filtration is repeated until the desired depletion rate is attained. It is also possible to set up several filters one behind the other, through which filtration successively takes place. After determining the depletion factor, the pyrogens introduced by the phages are eliminated by rinsing the cartridges with caustic soda solution. After neutralization, it is ready for use in the production process.

Surprisingly, it was found that the process according to the invention is especially suitable for using virus depletion during the production process in the preparation of sterile extracts from biological materials as a so-called in-process control. It was found that depletion of marker substances in the specimen to be purified is correlated with the depletion rate of the viruses. It is thus possible to follow virus depletion by determining the depletion of the marker substance.

The procedure according to the invention is that of determining the depletion rate of virus and marker and ascertaining the ratio of both depletion rates, i.e., a calibration curve is prepared from this, and the virus depletion is followed by means of the calibration curve in a continuous process.

Easily determined substances, which are preferably already present in the system to be purified, are usually used as markers. However, it is also possible to add marker substances to the system to be depleted. Preferred marker substances include proteins, peptides, and/or nucleic acids. However, it is also possible to introduce synthetic substances as markers, especially oligomers and polymers. Such polymers are known to experts and can be found for the system involved by simple, easy experiments. BSA is used according to the invention as an especially preferred marker.

Preferred preparations to be purified usually include biological materials, especially those from plant and animal organisms. Such preparations are preferably obtained from organs, tissues, and/or cells. Preferred organs include spleen, thymus, and/or bone marrow. However, the process according to the invention is also suitable for the purification of biological material obtained from body liquids or from bacterial or viral material, especially from pathogenic material.

The depletion factor is determined with four different viruses in a preferred form of execution according to the invention.

The invention is illustrated by the figures and the following examples.

Figure 1:
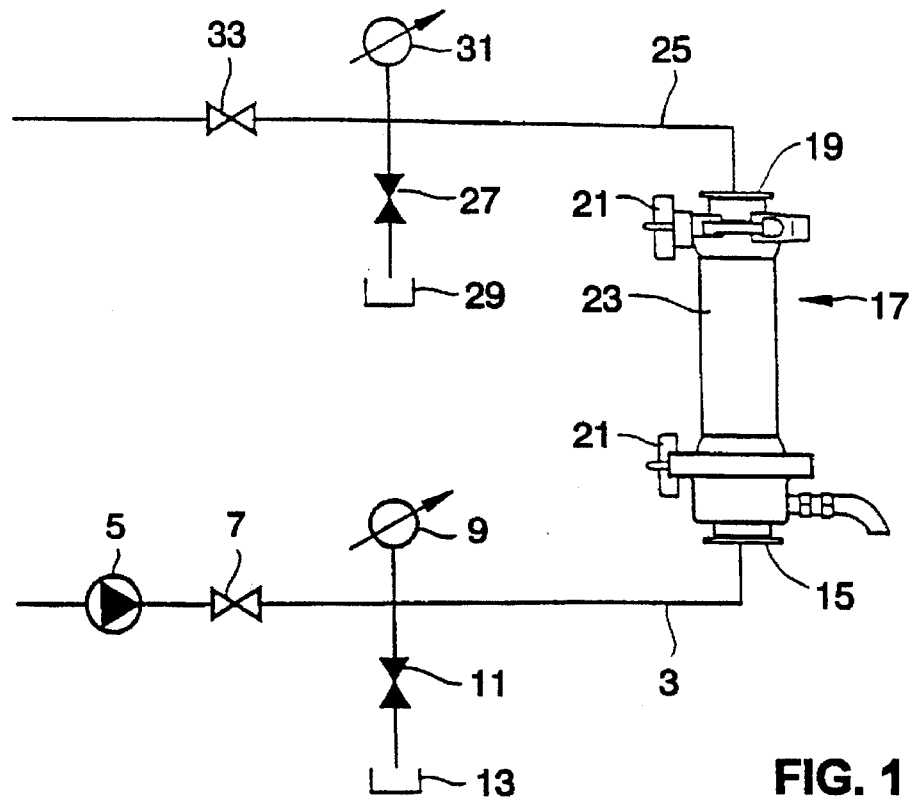
FIG. 1 shows the design of a filtration system which is on the market under the name Amicon S1.

FIG. 1 shows a filtration system for the ultrafiltration of organic solutions. The solution is conducted from a storage tank (not indicated) through line 3, which is equipped with rotary pump 5, throttle valve 7, manometer 9, shutoff valve 11, and discharge 13, through inlet 15 into filtration arrangement 17. Filtration arrangement 17, which is provided with inlet 15, outlet 19, and clamps 21, contains spiral cartridge 23. The filtrate passes from filtration arrangement 17 through line 25, provided with shutoff valve 27, outlet 29, manometer 31, and check valve 33, into another storage tank (not shown).

Figure 2:
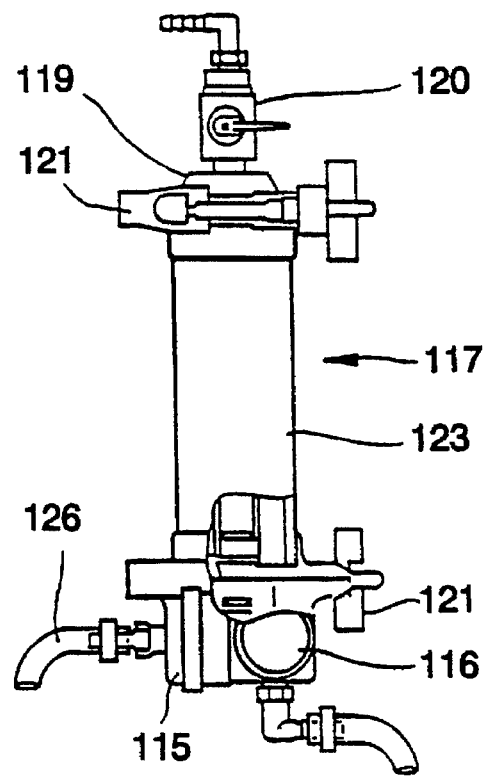
FIG. 2 shows a filtration cartridge of the filtration system of FIG. 1.

FIG. 2 shows filtration arrangement 117. Filtration arrangement 117 presents inlet 115, which is provided with manometer 116 and clamping device 121. Permeate port 126 leads into the inlet. Filtration arrangement 117 contains spiral cartridge 123. Outlet 119 is located at the upper part of filtration arrangement 117; it is provided with check valve 120 and clamping device 121.

EXAMPLE 1

Test for virus depletion of a Sartorius polysulfone membrane with a molecular exclusion of 100,000 daltons.

A polysulfone filtration box from Sartorius Co. (Göttingen, FGR) was inoculated with a phage suspension in tangential flow, with strict adherence to the conditions described in the prototype procedure. Table 1 presents the results of these test runs at 3 different partial pressures. The phage was depleted only by a power of 10 at all partial pressures. To attain a depletion by a factor of $10^{10}$, the filtration would thus have to be repeated at least 10 times, with this repetition controlled by inoculation with phage fr.

EXAMPLE 2

In this example, the virus depletion was tested by the Amicon S1 filtration system with an ultrafiltration membrane with a molecular exclusion of 30,000 daltons. The technical principle of the filtration system is represented in FIG. 1. The filtration cartridge is shown in FIG. 2. The solution to be filtered flows over the membrane in tangential flow. Part of the solution is filtered by transmembrane pressure ($P_t$) existing over the membrane. The pressure at inlet 15 (Pa) and at outlet 19 (Pb) of the unit can be read at two manometers. The transmission pressure forming over the membrane is calculated according to formula $$Pt = \frac{Pa + Pb}{2} - Pp$$

where Pp represents permeate pressure, which is usually equal to zero, and $\neq$ Pa. The specimens were pumped by peristaltic pump 31 into cartridge 23 at 130 rpm with an inner tube diameter of 8 mm. The transmission pressure was adjusted at 0.2, 0.4 and 0.7 bar by the drain valve.

To test the cartridge, phage solutions with a titer of $7.8 \times 10^9$ pfu (plaque-forming units) per ml (in 10 mM Tris-Cl buffer, pH 7.5, with 100 mM NaCl and 1 mg bovine serum albumin per ml) were pumped over the membrane. 1.5 L phage solution was filtered for each test. Between each filtration, the cartridge was cleaned with 0.1-M NaOH and then rinsed with phosphate-buffered NaCl solution until the eluate was neutralized. Phages remaining in the system were completely inactivated by this washing procedure. The cartridge was stored in 10 mM NaOH.

Table 2 contains the results of this test with filtration cartridge S1Y30 having serial number 8864. Depletions of 4.53 $\log_{10}$ were obtained immediately after operation start-up, and 4.4 $\log_{10}$ after storage in 10 mM NaOH for several months after the first filtration.

EXAMPLE 3

Determination of the depletion rate in an ultrafiltration unit with bacteriophage fr Spiral cartridge S1Y30, serial number 8864, of Amicon Co. was tested. For the purpose, 600 ml each of a phage suspension with an initial titer of $3 \times 10^{10}$ were filtered over the cartridge three successive times in five parallel runs. Between each filtration step, the cartridge was rinsed with 2 L RO water (water highly purified by reverse osmosis). Table 3 shows that no infectious phage fr is contained in 1 ml of the permeate in all five parallel runs after three filtrations over the cartridge.

EXAMPLE 4

Depletion of test viruses by factor 12

Filtration cartridge S1Y30, serial number 10330, was tested. The phage solution consisted of 600 ml phage buffer (methods) with 600 mg bovine serum albumin and 50 ml phage concentrate (titer: $1.3 \times 10^{12}$ pfu (plaque-forming units)/ml). The filtration was first done three successive times. The filtrate volume decreased from 600 to 400 and down to 380 ml. The filtration time for each step was about 20 minutes. The cartridge was washed with 1 L 10 mM caustic soda solution to inactivate phage residues between each filtration, and was then rinsed with distilled water until neutrality (as measured with pH electrode).

The virus contents in the individual filtrates were determined. They are shown in Table 4.

Since bacteriophage fr is no longer detectable in 1 ml filtrate after the second filtration, the last filtrate (380 ml) was again enriched with 40 ml virus concentrate (titer: $5.2 \times 10^{12}$ pfu/ml) and filtered three successive times. As is seen from Table 1, no further phages can be detected in 1 ml of filtrate after the second filtration.

It is seen from the virus depletion data (Table 4) that the virus titer decreased by 6.92 and 7.22 $\log_{10}$ after the first filtration with the ultrafiltration cartridge used. No further phages were detectable in the filtrate after the second filtration in all cases. The viruses were accordingly reduced by a total of 11 powers of ten after the first two filtrations, and by 11.7 powers of ten after the two further filtrations, from which a total reduction of 22.7 powers of ten after four filtrations is calculated. The depletion by 12 to 16 frequently recommended in the literature is already exceeded after three filtrations, with 18.22 powers of ten. The virus depletion in this production series is already better, with 7 $\log_{10}$, than in the production run used in Examples 2 and 3, with 4.5 $\log_{10}$ (Tables 3 and 4). Considerable differences in virus depletion between the individual production lots can thus be determined, which again underscore the need for careful validation with a test virus.

EXAMPLE 5

Monitoring virus depletion of a thymus extract by determining BSA

Calf thymus glands were removed and homogenized. An extract was obtained from this homogenate in a known way. Bacteriophage fr (ATCC No. 15767-B1; Knolle and Hoffman pub., Virology, vol. 123: 271–273, 1964) was added as test virus to the extract obtained. The BSA and purine and pyrimidine contents were determined by HPLC analysis in a usual way known to experts.

The specimen treated with the test phage was then filtered, as described in Examples 3 and 4, over filtration cartridge S1Y30 with serial number 10330 (Amicon Div.; W. R. Grace & Co.; Danvers, Mass., U.S.A.), and the virus depletion as well as BSA decrease were determined. The virus decrease was correlated with the BSA decrease.

Bacteriophage fr (ATCC 15767-B1) was filed on Nov. 19, 1964 with the American Type Culture Collection, 12301 Parklawn Drive, Rockville, Md. 20852-1776, U.S.A. It has been freely available on the market since Nov. 19, 1964.

E. coli 3300 (ATCC 19853) was filed on Jan. 12, 1967 with the American Type Culture Collection, 12301 Parklawn Drive, Rockville, Md. 20852-1776, U.S.A. It has been freely available on the market since Jan. 12, 1967.

TABLE 1

Ultrafiltration with the Sartorius tangential flow system
Ultrafilter: Polysulfone membrane with a molecular cutoff of 100,000 daltons
Module type: 303 145 69 01 W
Test conditions:
First run: Permeate flow - 4 ml/sec, partial pressure - 0.8 bar
Eluate volume: 660 ml, filtration duration: 2 min. 31 sec
Concentrate volume: 66 ml
Second run: Permeate flow - 2.3 ml/sec., partial pressure - 0.4 bar. Volume of eluate and concentrate as above, filtration duration: 4 min. 32 sec
Third run: Permeate flow - 5 ml/sec, partial pressure - 1.6 bar volume of eluate and concentrate as above, filtration duration: 1 min. 56 sec Distribution of bacteriophages:

| No. | Initial solution pfu/ml | Concentrate pfu/ml | Permeate pfu/ml | Phage elimination rate ($\log_{10}$ pfu1/pfu2) |
|---|---|---|---|---|
| 1 | 4.30E + 06 | 5.00E + 06 | 1.80E + 05 | 1.378196 |
| 2 | 4.30E + 06 | 6.35E + 06 | 1.50E + 05 | 1.4573772 |
| 3 | 1.70E + 09 | 7.40E + 09 | 1.60E + 08 | 1.0263289 |

TABLE 2

Test of Amicon S1Y30 ultrafiltration system for permeability for test phage fr
1.5 ml each of a phase test solution (bacteriophage fr in 10 mM Tris-Cl, pH 7.5, 100 ml NaCl and 1 mg bovine serum albumin per ml) was filtered over the spiral cartridge at the specified transmission pressures.

| | First filtration*) | | | Second filtration*) | | |
|---|---|---|---|---|---|---|
| Transmission pressure | Filtration solution | Permeate | Concentrate (10% of the initial solution) | Solution before filtration | Permeate | Concentrate (10% of the initial solution) |
| 3 psi | $7.8 \times 10^9$ | $2.3 \times 10^5$ | $1.3 \times 10^{10}$ | $2.3 \times 10^5$ | 0 | $9.6 \times 10^5$ |
| 6 psi | $7.8 \times 10^9$ | $6.9 \times 10^5$ | $6.4 \times 10^9$ | $6.9 \times 10^5$ | $1.5 \times 10^1$ | $2.8 \times 10^6$ |
| 10 psi | $7.8 \times 10^9$ | $7.3 \times 10^5$ | $1.07 \times 10^{10}$ | $7.3 \times 10^5$ | $1.5 \times 10^1$ | $3.3 \times 10^6$ |

*)The phage titer is give in plaque-forming units (pfu) per ml.

TABLE 3

Validation of ultrafiltration cartridge S1Y30 with test phage fr a)

Titer of test phage fr in plaque-forming units b) per ml (pfu/ml)

|  | In the initial solution | In the permeate of the first filtration | In the permeate of the second filtration | In the permeate of the third filtration |
|---|---|---|---|---|
| First test run | $3 \times 10^{10}$ | $3.4 \times 10^6$ | $2.9 \times 10^2$ | 0 |
| Second test run | $3 \times 10^{10}$ | $4.5 \times 10^6$ | $7.3 \times 10^1$ | 0 |
| Third test run | $3 \times 10^{10}$ | $3.9 \times 10^6$ | $1.1 \times 10^2$ | 0 |
| Fourth test run | $3 \times 10^{10}$ | $7.0 \times 10^6$ | $7.0 \times 10^1$ | 0 |
| Fifth test run | $3 \times 10^{10}$ | $5.4 \times 10^6$ | $7.6 \times 10^1$ | 0 |
| Mean values |  | $4.84 \times 10^6$ | $1.24 \times 10^2$ |  |
| Standard deviations |  | $1.2 \times 10^6$ | $8.4 \times 10^1$ |  | a) 600 ml each of phage test solution (bacteriophage fr in phage buffer: 10 mM Tris-Cl, 10 mM $CaCl_2$, 0.15M NaCl, and 1 mg bovine serum albumin per ml) was filtered three successive times over Amicon ultrafiltration cartridge S1Y30 at a transmission pressure of 3 psi.
b) The titer of the phages was determined with *Escherichia coli* strain 3300 on agar plates after the technique described by Davis and Sinsheimer (Top Agar Method, J. Mol. Bio. 2:203–207, 1963). The permeates were diluted in phage buffer (see (a)). In a deviation from the original specification, the titration was done on Luria-Bertani culture medium (10 g trypton, 5 g yeast extract, 5 g NaCl in 1 L RO water, pH adjusted to 7.5 with NaOH). Moreover, 3 mM $CaCl_2$ was added to the top agar.

TABLE 4

Virus titers in filtrates of the individual filtration steps with the Amicon S1Y30 ultrafiltration cartridge

| Filtration step | Virus titer (pfu/ml) |
|---|---|
| Initial solution | $1 \times 10^{11}$ |
| First filtration | $1.2 \times 10^4$ |
| Second filtration | 0 |
| Third filtration | 0 |
| Addition of new test phages | $5 \times 10^{11}$ |
| First filtration | $3 \times 10^4$ |
| Second filtration | 0 |
| Third filtration | 0 |

I claim:

1. A method of depleting pathogens in a solution or suspension of organic material which comprises:
    (a) calibrating a removal rate of an ultrafilter or ultrafiltration unit by introducing at least one test virus comprising a leviviridae virus or another bacteriophage of equivalent size through the ultrafiltration apparatus;
    (b) determining the titer of virus before and after ultrafiltration;
    (c) calculating the removal rate from (b); and
    (d) passing the organic material through the ultrafiltration apparatus comprising an ultrafilter or ultrafiltration unit the removal rate of which was previously determined, thereby depleting pathogens in the solution or suspension of organic material.

2. The method of claim 1, wherein the test virus is selected from the group consisting of the MS2, f2, f4, fr, Qβ, Vk, ST or R17 viruses.

3. The method of claim 2, wherein the test virus is the fr virus (ATCC No. 15767-B1).

4. The method of claim 1, wherein a solution or suspension of the test virus is ultra-filtrated under precisely defined pressure conditions, and the solution or suspension of organic material is ultra-filtrated under the same conditions.

5. The method of claim 1, wherein the organic material is derived from plants, animal tissues or organs, bacteria samples or virus samples.

6. The method of claim 5, wherein the animal tissues or organs are spleen, thymus or bone marrow.

7. The method of claim 1, wherein a marker substance is added to the solution or suspension of organic material, the removal rate of the marker substance during ultrafiltration is determined, the ratio of the removal rates of the marker substance and test virus are determined and the rate of removal of the virus from the solution or suspension is controlled by controlling the rate of removal of the marker substance.

8. The method of claim 7, wherein the marker substance is a protein.

9. The method of claim 8, wherein the protein is bovine serum albumin.

10. The method of claim 7, wherein the marker substance is a nucleic acid molecule.

11. The method of claim 1, wherein the pathogens are viruses.

12. The method of claim 1 wherein the ultrafilter or ultrafiltration unit is selected from a group consisting of a Sartorius polysulfone membrane with a molecular exclusion of 10,000 daltons and an Amicon S1Y30 filtration system with an ultrafiltration membrane with a molecular exclusion of 30,000 daltons.

13. A method of determining a rate of removal of viruses from a solution or suspension of organic material which comprises adding a known amount of a leviviridae virus to the organic material, purifying the organic material of the leviviridae virus, determining the amount of virus remaining in the organic material after purification and comparing the amount of leviviridae virus in the organic material before and after purification to determine the removal rate of the virus.

14. The method of claim 13, wherein a marker substance is added to the solution or suspension of organic material, the removal rate of the marker substance during purification of the organic material is determined, the ratio of the removal rates of the marker substance and leviviridae virus are determined and the rate of removal of the leviviridae virus from the organic material is controlled by controlling the rate of removal of the marker substance.

15. The method of claim 14, wherein the marker substance is a protein.

16. The method of claim 15, wherein the protein is bovine serum albumin.

17. The method of claim 14, wherein the marker substance is a nucleic acid molecule.

18. The method of claim 13, wherein the organic material is derived from plants, animal tissues or organs, bacteria samples or virus samples.

19. The method of claim 18, wherein the animal tissues or organs are spleen, thymus or bone marrow.

20. The method of claim 13 wherein the ultrafilter or ultrafiltration unit is selected from a group consisting of a Sartorius polysulfone membrane with a molecular exclusion of 10,000 daltons and an Amicon S1Y30 filtration system with an ultrafiltration membrane with a molecular exclusion of 30,000 daltons.

* * * * *